(12) United States Patent
De Smet

(10) Patent No.: US 8,173,964 B2
(45) Date of Patent: May 8, 2012

(54) DEVICE FOR NON-DESTRUCTIVE TESTING OF A COMPONENT BY ANALYZING GENERATED RADIATION

(75) Inventor: Marie-Anne De Smet, Monbrun (FR)

(73) Assignee: Airbus Operations SAS, Toulouse (FR)

( * ) Notice: Subject to any disclaimer, the term of this patent is extended or adjusted under 35 U.S.C. 154(b) by 624 days.

(21) Appl. No.: 12/301,646

(22) PCT Filed: May 16, 2007

(86) PCT No.: PCT/EP2007/054762
§ 371 (c)(1),
(2), (4) Date: Jun. 23, 2009

(87) PCT Pub. No.: WO2007/135059
PCT Pub. Date: Nov. 29, 2007

(65) Prior Publication Data
US 2010/0011861 A1    Jan. 21, 2010

(30) Foreign Application Priority Data
May 24, 2006   (FR) ...................................... 06 51902

(51) Int. Cl.
*G01T 1/24* (2006.01)
*G01T 1/161* (2006.01)
(52) U.S. Cl. .......................... 250/331; 250/332; 73/783
(58) Field of Classification Search .................. 250/331, 250/332; 73/783, 788, 800, 802; 374/46
See application file for complete search history.

(56) References Cited

U.S. PATENT DOCUMENTS

| 3,511,086 A | 5/1970 | Woodmansee |
| 3,970,074 A | 7/1976 | Mogos et al. |
| 4,433,637 A | 2/1984 | Buirley et al. |
| 5,047,719 A | 9/1991 | Johnson et al. |

(Continued)

FOREIGN PATENT DOCUMENTS
DE    4220544 A1    1/1994
(Continued)

OTHER PUBLICATIONS

International Search Report dated Aug. 14, 2007.

*Primary Examiner* — Tony Ko
(74) *Attorney, Agent, or Firm* — Perman & Green, LLP

(57) ABSTRACT

A device for non-destructive testing of a component by analyzing radiation dissipation when the component is stressed by mechanical stresses. The device includes measuring means for determining a surface radiation field of the component. The measuring means are integrated in a flexible housing for covering a region of the surface of the component to be tested. The device enables an initial crack upon stress concentration on a surface of the component and the presence of a crack upon propagation of the crack to be detected. The disclosed embodiments are useful for non-destructive testing of aircraft components, but may be used in all industrial sectors where testing the integrity of components is important, such as the automotive, railway, marine and nuclear industries.

28 Claims, 3 Drawing Sheets

U.S. PATENT DOCUMENTS

| | | | |
|---|---|---|---|
| 5,659,248 A | 8/1997 | Hedengren et al. | |
| 6,077,228 A | 6/2000 | Schonberger | |
| 6,917,026 B2 * | 7/2005 | Yasuda et al. | 250/208.1 |
| 7,039,326 B1 * | 5/2006 | Chung | 398/202 |
| 2001/0015643 A1 | 8/2001 | Goldfine et al. | |
| 2003/0031296 A1 | 2/2003 | Hoheisel | |
| 2004/0016886 A1 * | 1/2004 | Ringermacher et al. | 250/370.11 |
| 2005/0062470 A1 | 3/2005 | Shoki | |

FOREIGN PATENT DOCUMENTS

| | | |
|---|---|---|
| EP | 0245147 A | 11/1987 |
| EP | 0577244 A2 | 1/1994 |
| EP | 0672380 A | 9/1995 |
| EP | 0887642 A1 | 12/1998 |
| EP | 1403635 A | 3/2004 |
| FR | 2836994 A1 | 9/2003 |

* cited by examiner

DEVICE FOR NON-DESTRUCTIVE TESTING OF A COMPONENT BY ANALYZING GENERATED RADIATION

CROSS REFERENCE TO RELATED APPLICATIONS

This application is the National Stage of International Application No. PCT/EP2007/054762 International Filing Date, 16 May 2007, which designated the United States of America, and which International Application was published under PCT Article 21 (2) as WO Publication No. WO2007/135059 and which claims priority from French Application No. 0651902, filed on 24 May 2006, the disclosures of which are incorporated herein by reference in their entireties.

This application is also related to U.S. patent application Ser. No. 12/301,702, filed on Jun. 23, 2009, (International Application Serial No. PCT/EP2007/054759) and U.S. patent application Ser. No. 12/301,701, filed on Jun. 23, 2009, (International Application Serial No. PCT/EP2007/054751) the disclosures of which are incorporated herein by reference in their entireties.

BACKGROUND

1. Field

The disclosed embodiments relate to a device for non-destructive testing of a component by analyzing the radiation dissipation when the component is stressed by mechanical stresses. Said device comprises measuring means for determining a surface radiation field of the component. The measuring means are integrated in a flexible housing for covering a region of the surface of the component to be tested. Said device enables an initial crack upon stress concentration on a surface of the component and the presence of a crack upon propagation of said crack to be detected. The disclosed embodiments is useful for non-destructive testing (NDT) of aircraft components, but may be used in all industrial sectors where testing the integrity of components is important, such as the automotive, railway, marine, and nuclear industries.

2. Brief Description of Related Developments

Within the design and qualification arena, as well as in the operation and maintenance of aircraft, it is necessary to employ testing methods that allow the evaluation of the stresses that the components will undergo and to be able to determine whether they have been damaged by cracks or fissures, without harming the components constituting the aircraft structure. The techniques used are jointly referred to as "non-destructive testing" (NDT). NDT techniques are numerous and constantly changing, because the industrial sectors concerned have a need for improved performance from these NDT techniques. The air-transport and civil-engineering sectors are always on the lookout for ever more effective NDT techniques to meet the dual requirements of safety and their desire for cost-reduction.

Therefore, the disclosed embodiments have for its particular purpose the detection of fissures that are beginning in the components submitted to strong mechanical and cyclical stresses the repetitions of which after a certain period of time, lead to so-called fatigue cracking and which may lead to breakage of the component.

Among the various NDT structural techniques, the stimulated infrared thermography technique is known for detecting defects in aeronautical structures while based on thermal detection of thermal diffusion barriers constituted by the cracks. This technique consists of rapidly heating the surface of the material to be tested for example by using a flash lamp and observing the surface radiation field with an infrared camera for example. The presence of a defect or a crack appears locally on the thermography images by an abnormally slow return to the room temperature in one area of the component.

SUMMARY

FIG. 1 shows a schematic diagram of a device pertinent to this technique. The device includes a laser (16) which locally irradiates a zone A on the surface of a component to be tested (4) and an infra-red detector (9) which observes a zone B located near zone A for elevations in the temperature produced by heating of zone A. These elevations are influenced by the local characteristics of zone B and by its proximity of the inspected material. Specifically, the presence of a thermal barrier produced by a crack (5) inside the component (4) acts on the heat diffusion within the component by thermal conduction. To obtain a map of the temperature field of the component's surface (4), the device includes a scanning system made up of adjustable motorized mirrors (17) to guide the incidental excitation beam (19) and the beam probes (18).

In a device such as that presented in FIG. 1, an operator moves from zone to zone to examine the entire surface of the structure to be tested. Therefore it is necessary to immobilize the structure which may be, for example, an airplane on the ground during an inspection, and must call upon qualified personnel to carry out these monitoring operations, involving high costs of maintenance for the airline company. Trained and qualified operators are indeed necessary to carry out quality control and to avoid erroneous interpretations of the thermography obtained.

Moreover, this device does not make it possible to easily test the components on a relatively extensive surface, because it is necessary for the operator to move the device from zone to zone. To be able to control certain complex structural or pipe fittings comprising the inaccessible zones, sometimes it is necessary to disassemble the structure. Especially the cracks which for example, begin in bores or connecting systems, may only be detected when they open directly onto an accessible surface.

Currently, there is no means for inspecting the status of structures, e.g., aeronautical components, throughout their periods of use, and in particular for carrying out an overall evaluation of the health of aeronautical components while the airplane is in flight.

The disclosed embodiments attempt to propose a device suited to such an inspection, which enables monitoring of the state of fatigue in components that characterizes conformity of the structures in relation to the specifications in the different life stages of an aircraft.

The problems faced by such a device are:

to provide a means for non-destructive testing adapted to be easily connected to the surface of the components to be tested while remaining of a negligible mass and size and by requiring only low electric power for its operation, it could even be self-powering.

to provide a method for testing adapted to be permanently installed on the components to be tested during their use to perform predictive maintenance by detecting anomalies as soon as possible, thus allowing less expensive repairs to be performed and to guarantee maximum safety of the components, to provide a means of testing that enables automatic management of the inspections and that provides a full analysis of the components' health, so as to reduce the operator's work as much as possible in order to reduce the cost of maintenance.

For this purpose, the disclosed embodiments concern a non-destructive testing device in real time by analysis of the dissipation of thermal radiation, x-rays, or gamma rays emitted by the surface of the component when it is stressed by mechanical stresses.

According to the disclosed embodiments, the device contains means for measuring suitable for determining a radiation field on the surface of the component, said means of measuring being incorporated in a housing designed for covering the surface of said component.

Advantageously the aforementioned support is a flexible support in order to take on the shape of the component.

The aforementioned means of measurement are adapted to be sensitive to determining a field with an elevation in the radiation intensity caused by defects found in the component.

In a specific embodiment, the means of measurement includes a network of radiation microsensors organized in a matrix of lines and columns. To transform the radiation received by the microsensors into electrical signals, each microsensor includes a cell capable of transforming the radiation received into electrical charges, said cell being coupled with an electrical charge transfer device to collect electrical charges.

In another embodiment, the means of detection and measurement includes a thermosensitive liquid crystal membrane, and a network of opto-electronic microsensors superimposed on said thermosensitive liquid crystal membrane. The opto-electronic microsensors is organized in a matrix of lines and columns. Each opto-electronic microsensor includes a photosensitive cell to transform the optical signals sent by the membrane in electric signals, said cell is coupled to a charge transfer device to collect electric signals.

According to one embodiment, the testing device also contains an interface electronics connecting said means of detection and measurement to a recording memory, said interface electronics and said memory also being incorporated into said flexible housing so as to advantageously form a monolithic testing device.

The testing device advantageously contains a calculating system such as a microprocessor system to automatically identify an elevation in the radiation energy field on the surface of the component.

According to one embodiment, the calculating system is not incorporated into the flexible housing, said testing device contains a means of transmitting, to send the electrical signals recorded in the recording memory to said calculating system by using a radio or infrared wired or wireless link.

In another embodiment, said calculating system is incorporated into the said flexible housing and is connected between said interface and said recording memory.

According to one embodiment of the calculating system, it includes a memory containing at least one reference map of the radiation field on the reference surface of the component(s), a means of calculation for converting the electrical signals received by said calculating system in the radiation field, and means for analysis of said radiation field through comparison with the reference radiation field.

The means for analysis includes the means for differential analysis to determine a radiation field differential between the reference radiation field and the measured radiation field.

Advantageously, said means for differential analysis included means for generating a status signal S, characteristic of the fact that said radiation field differential value exceeds a threshold value.

The means for analysis includes means for spectral analysis to determine the information relative to the defects present in the component.

Advantageously, according to the status signal S and the information transmitted either by said calculating system to a means of alarm or recorded in the recording memory linked to said calculating system, then sent to the means of alarm by using a wired or wireless radio or infrared link.

The means of alarm may contain a display panel and light or sound indicators.

In another embodiment, said microsensors are directly integrated in a lining layer for covering a surface of the component to be tested.

Other characteristics and advantages of the disclosed embodiments will be better understood by reading the following description and referring to the drawings, which show:

DETAILED DESCRIPTION OF THE DISCLOSED EMBODIMENTS

Three phases during the break-up of a component are distinguished. In the first period, the defects form in a diffuse manner in the zones that are the most stressed, by mechanical stresses or deformations applied to the component. In the second period, these defects evolve or coalesce and a macroscopic break appears that is propagated in the third period until it leads to the break-up of the component. These three phases are accompanied by thermal dissipation. Dissipated thermal energy is proportional to the concentration of the stress. Thermal dissipation is greater in the zones which are more stressed mechanically. Furthermore, when the material develops a fissure, the crack in the fissure is located using a localized rise in temperature. The front portions of the fissures constitute the hot points. By establishing a surface temperature field map of a component and by implementing the adjusted means for analysis, the zones may be located where there is an elevation of the temperature representative of the dissipated thermal energy.

Figure 1:
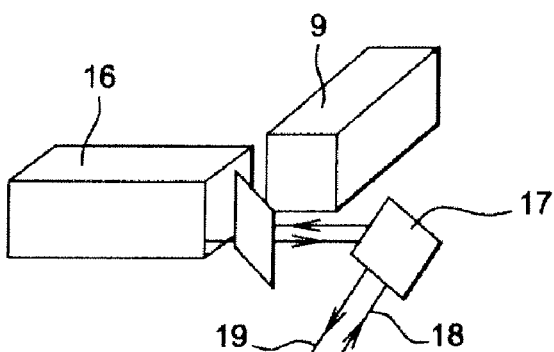
In FIG. 1: A schematic diagram of a thermograph device of the prior art.
Figure 2:
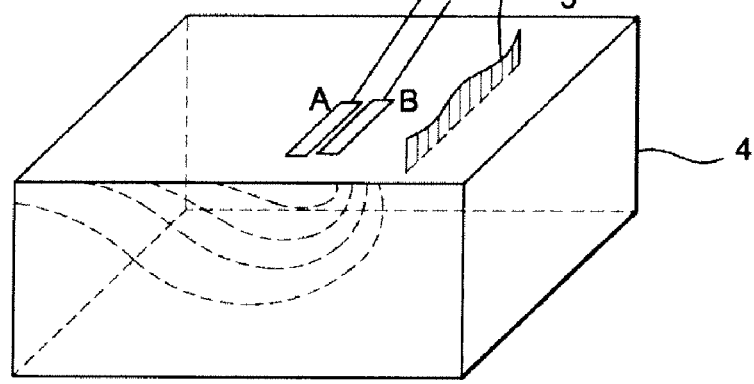
In FIG. 2: A schematic cross-section view of a device according to one embodiment In FIG. 3: A schematic cross-section view of a device according to another embodiment, In FIG. 4: A partial schematic cross-section view of the top of the testing device, In FIG. 5: a schematic diagram of the testing device from FIG. 4 in operating position for transmitting electrical signals to a remote calculating system, In FIG. 6: a schematic diagram of a network of testing devices arranged on the surface of the structures of an airplane on the ground, in position to transmit the signals recorded while the plane was in flight.
Figure 2:
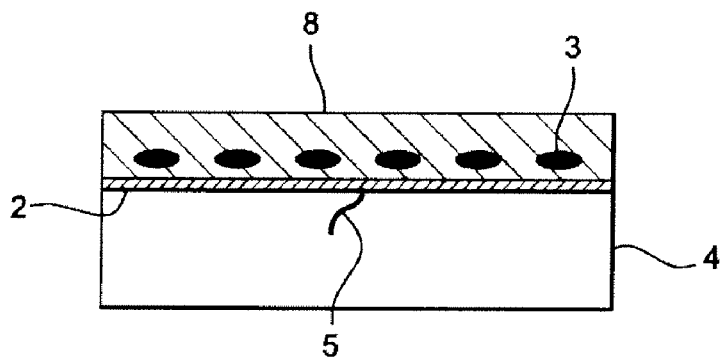
Figure 3:
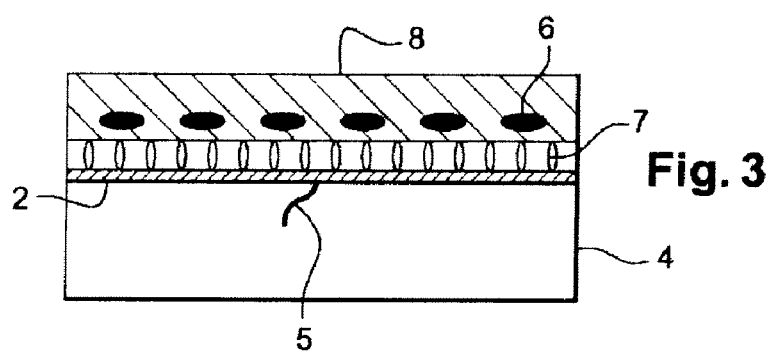

FIGS. 2 and 3 show two embodiments of a device for real time non-destructive testing (1) of a component by analyzing radiation dissipation when the component is stressed by mechanical stresses. It includes measuring means capable of determining a surface radiation field of the component, said means are incorporated in a flexible housing (2). This flexible housing (2) may for example be made of a plastic material enabling the device to be attached to the surface of the component to be tested, by following the shape of the structure. The flexible housing of the testing device (1) is fixed to the surface of the structure to be tested by means of an adhesive material. This device should preferably be produced in a limited adjustable size to be attached to a critical area of the component where cracks are liable to appear. On an aircraft, the device may be placed on areas regarded as critical, located for example where the elements are attached, at the level of the assembly elements of the panels, and in areas where there is a strong concentration of stress.

In a general way, the type of radiation dissipated by the component may be infrared, x-rays, or gamma rays.

Advantageously, this testing device (1) is designed to receive a surface coating (8), which may for example be a coat of paint that covers testing device (1).

In FIG. 2 the first embodiment of means of measurement is shown including a radiation microsensor network (3) that is incorporated in a flexible housing (2) fixed on the surface of the component to be tested (4). Each radiation microsensor (3) is capable of transforming the flow of radiation which may be infrared or x-ray or gamma rays emitted by the component (4) in the form of electrical signals through a cell that converts the energy of the radiation into an electrical charge. Each cell is coupled to a charge transfer device that has for its function to evacuate the electrical charge. An electrical signal representative of the radiation energy received by the cell is thus generated by the charge.

In FIG. 3, a second embodiment of the means of measuring includes a thermosensitive liquid crystal membrane (7), and a network of opto-electronic microsensors (6) superimposed on the thermosensitive liquid crystal membrane (7). The thermosensitive liquid crystal membrane is made up of liquid crystals inserted between two plastic surfaces. The structure of these liquid crystals is modified by the thermal energy received, that is translated by a variation in the spectral composition of the waves reflected by the different planes of the liquid crystals, consequently leading to a change in color on the surface of the liquid crystal membrane (7).

To detect this change in color in terms of the radiation energy level, a network of opto-electronic microsensors is superimposed on this membrane. Each opto-electronic microsensor is capable of transforming the luminous radiation emitted by the liquid crystal membrane into electronic charges through a photosensitive cell that converts light energy into an electric charge. Each cell is coupled to a charge transfer device that has for its function to evacuate the electrical charge. An electrical signal representative of the luminous energy received by the photosensitive cell is thus generated by the charge.

Figure 4:
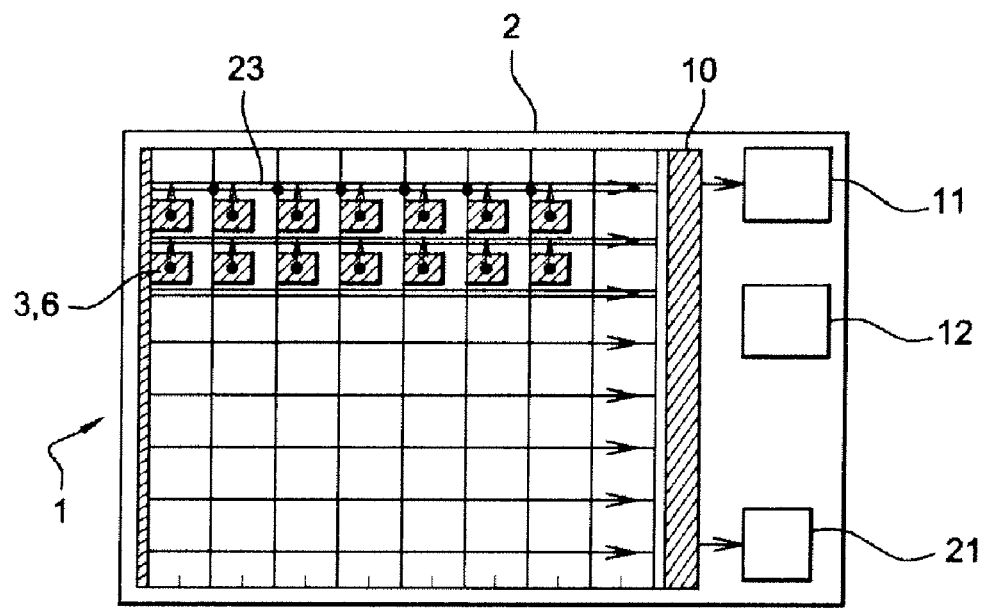
Figure 5:
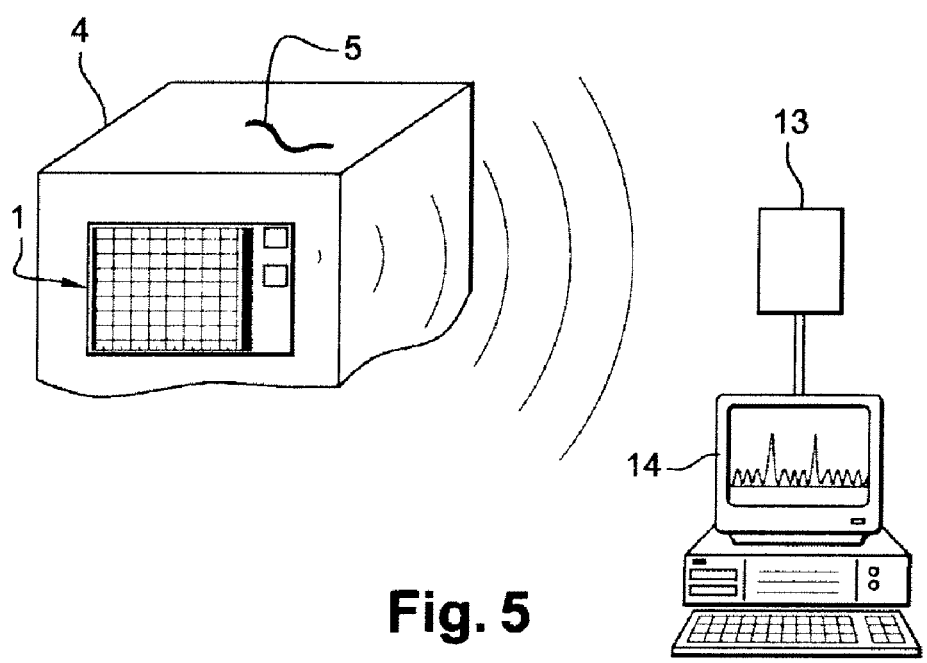

FIG. 4 is a schematic diagram of a top view of the test device according to the embodiments presented previously. According to one specific embodiment the device has a rectangular form including here, as an illustration, a network of 56 radiation or opto-electronic microsensors organized in a matrix of lines and columns. The testing device also contains an interface electronics (10) connecting the microsensor network (3, 6) to a recording memory (11). The electronics (10) and the memory (11) are also incorporated into the flexible housing (2) so as to advantageously provide a monolithic testing device.

The electrical charges collected by the charge transfer devices of each microsensor are transmitted to the electronic interface assembly (10) that includes an amplifier to increase the power of the signal in order to improve the Signal to Noise Ratio and also a digital/analog converter to convert the analog electric signals received into digital signals.

The amplified signals are then sent to the recording memory (11). The interface electronics (10) are placed at the end of the microsensor lines in the shown in FIG. 4. In another embodiment, the electronics of the interface (10) might be placed at the end of the microsensor columns.

The organization of the microsensors in the matrix of lines and columns enables obtaining a radiation field map of the type that a defect in the component may be located on the surface of the component.

In order to locate the defects precisely, the spacing between microsensors is preferably set at a value lower than the minimum size of the defects to be detected, such that the position of the defects can be determined, and such that in the event of local damage to the microsensor network the microsensors located around the damaged area will always allow monitoring of the areas closest to a possible equipment defect in the monitored area.

In one specific embodiment the mode of transfer of the electrical signals coming from the microsensors (3, 6) to the interface electronics (10) is an interlinear transfer mode. Above each line of microsensors there is a storage line 23. The signals are temporarily stored in this storage line 23. The content of the storage lines is then transferred to the interface electronics (10) in parallel mode. The electronic signals are then removed in series to a recording memory (11).

In a variant of the electrical-signal transfer mode, each microsensor is addressed directly to send its electric signals directly to the interface electronics (10).

In order to automatically process the electric signals measured by the microsensors, the control device also includes a calculating system (13) to convert the electric signal into a representative signal energy of the radiation dissipated by the surface of the component and to determine a radiation field of the component. The calculating system may be a microprocessor system.

In a preferred embodiment, shown in FIG. 4, since the calculating system is not incorporated into the flexible housing (2), the device contains a means of transmission, (12) to send the electrical signals recorded in the recording memory (11) to the calculating system (13) by using a wireless radio or infrared link. This means of transmission contains for example a transponder integrated into the flexible support, which preferably operates on a fixed frequency, said frequency being chosen so that the transmission of the electrical signals representing the dissipation of the radiation energy on the surface of the component does not interfere with the transmission of other data by devices other than the testing device (1).

The transmission means (12) for sending the recorded electric signals in the memory (11) to the calculating system (13) may also be a wired link.

The electric signal received by the calculating system (13) is converted into a signal representative of the radiation energy dissipated by the surface of the component due to the calculation means in which is integrated an adapted theoretical model linking the energy to the electric charge. These means of calculating generating the mapping of the radiation field that may be an amplitude and phase map, and a spectral map. This data representing the energy dissipated by the component is then sent to the analysis means.

The means for analysis includes means for differential analysis to perform a comparative amplitude study between the radiation field measured by the microsensor network and the reference radiation field. Advantageously, this differential analysis means enables the establishment of a field map of an elevated radiation energy level on the surface of the component. For this purpose the calculating system contains a memory in which a database of reference radiation field maps of the component is recorded. These reference mappings constitute a predefined model for comparison with the behavior of the area covered by the testing device.

This reference mapping can be predetermined on a reference component. "Reference component" means a component considered not to contain any defect, e.g., a component leaving the end of its production line, having successfully completed all the qualification stages. They may also be predetermined by modeling. When the means of analysis perform an amplitude comparison between the reference radiation field and the radiation field measured by the microsensors, if the calculated differential value between the reference radiation field and the measured radiation field exceeds a threshold value, a status signal S is generated by the means of analysis.

Advantageously, the means for analysis includes means for spectral analysis that determines a spectral representation of the measured radiation field for determining the information relative to the defects present in the component. Specifically, the spectral analysis enables determination of the nature of the defects and their size.

Within the framework of real-time testing of the structures, the testing device may for example be programmed to be activated while the aircraft is no longer on the ground and it then performs measurements at regular intervals, e.g., every 5 minutes over a predetermined period so as to perform time-based measurements. In this way the testing device enables a mapping of the area monitored over time, to define the development of the radiation field emitted by the component.

Time-based measurements enable the performance of a contrast temporal development analysis of the energy level from which the depth may be identified of the defect which created this contrast.

The status signals as well as all information such as the nature of the defects, the size of the defects, and the locations of the defects are sent by the calculation system to the means of alarm (14) which may include a display panel (22) to show the information and light and/or sound indicators (20) to warn the maintenance operator.

Figure 6:
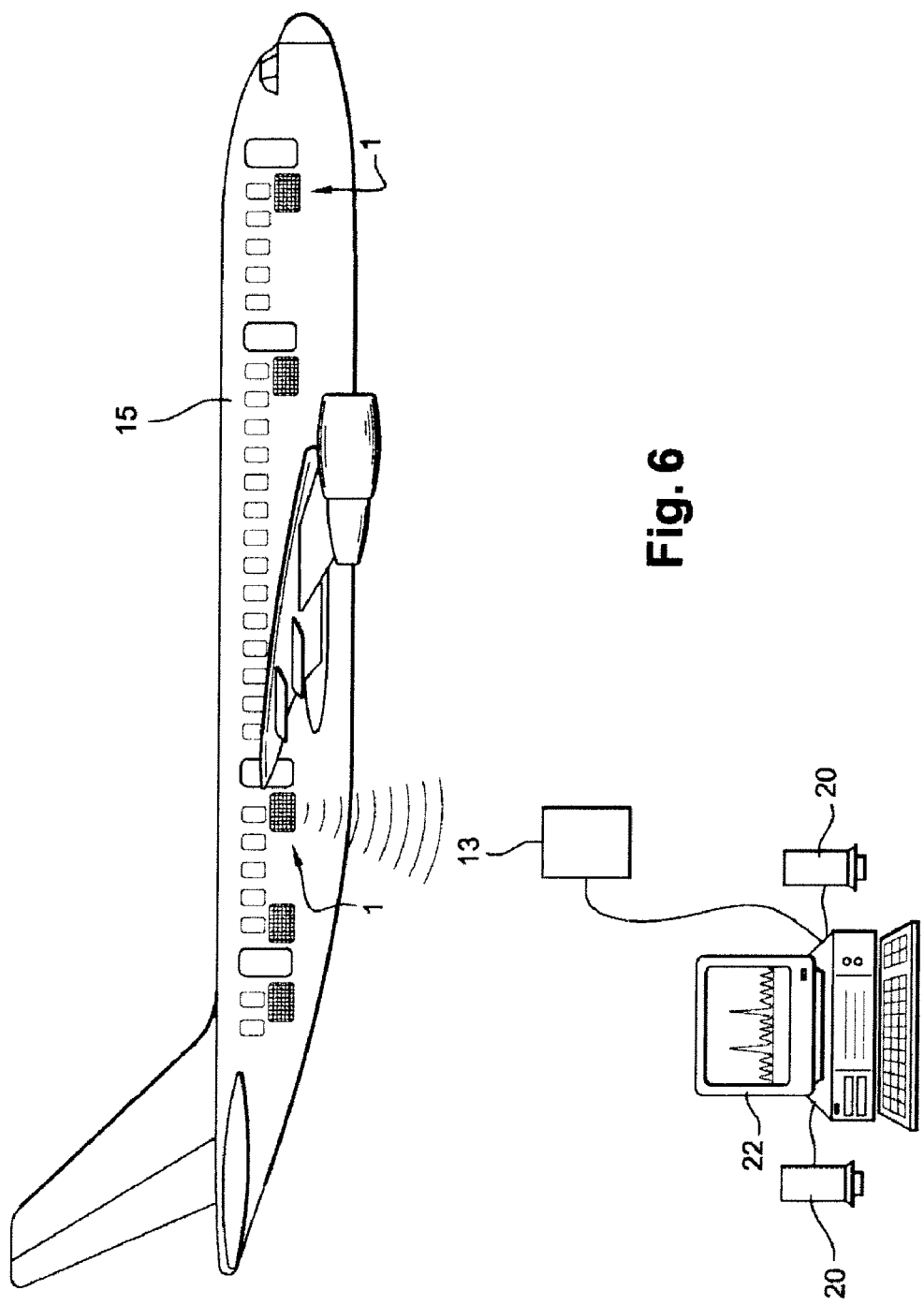

One example of the mode of signal transmission is shown in FIG. 6 which is a schematic view of a network of several testing devices (1) arranged on the surfaces of the structures of an aircraft (15).

The airplane is on the ground and the network of testing devices (1) is in the position for transmitting the signals recorded during one or more flights by the aircraft to a calculating system (13), which is connected to a means of alarm (14); here, these include a computer with a monitor (22) and sound indicators (20).

Advantageously, the calculation system sends the radiation energy elevation field level of the component tested to the monitor in the form of a color-coded image thus enabling the operator to quickly find the areas where the radiation energy level is raised and likely to reveal the presence of defects.

The transmission of electrical signals recorded in the memory (11) to the calculating system can be programmed so that it is carried out automatically, for example at the end of an aircraft's flight. This transmission can also be activated manually by the maintenance operator, by querying the testing device during inspection of the plane.

In another embodiment, the calculating system (13) is directly incorporated into the flexible housing (2) and connected between the interface electronics (10) and the recording memory (11). In this embodiment, the calculating system (13) receives the electrical signals directly from the interface electronics (10) and sends only the status signals and information on defects to the recording memory (11). During an inspection, by querying the device, the operator downloads the status signals and the information recorded in the testing device's memory to the means of alarm (14) by using a radio or infrared wired or wireless link.

All the components incorporated in the flexible housing are produced by a micro-manufacturing technology on a hard substrate, transposed here on a flexible substrate such as a plastic substrate. However, the temperature used during the course of micro-manufacturing process is likely to destroy the plastic substrate. One of the solutions currently proposed consists of producing the components first on a hard substrate, itself deposited on glass. The hard substrate may be, for example, made of silicon, of aluminum, $Al_2O_3$. Another layer of glass to serve as protection is then fixed onto the components with a soluble adhesive, and the hard substrate is then removed from the stack by ablation with a laser.

The components are applied to a plastic substrate and fixed to it with a permanent adhesive, and the protective glass is removed.

In one specific embodiment, the testing device is presented in the form of a thin film having a thickness of around 50 μm, and a surface of 10×10 cm sideways that integrates the microsensor with a size of about one hundred micron, with a step of around ten micron.

The disclosed embodiments were presented within the framework of testing aircraft structures, but may be used in any industrial sector where testing the integrity of workpieces is important, such as the automotive, railroad, naval-construction, or nuclear sectors.

The invention claimed is:

1. A non-destructive testing device for testing a component by analyzing radiation generated by the component while the component is stressed by mechanical stresses, wherein said device comprises means for measurement capable of determining a radiation field generated by a surface of said component, said means for measurement being incorporated into a flexible housing designed to cover the surface of said component to be tested and of molding to a form of the component.

2. A testing device according to claim 1, wherein a sensitivity of said means for measurement is adapted to determine variations in radiation energy levels caused by a presence of defects in the surface of said component.

3. A testing device according to claim 1, wherein said means for measurement includes a network of microsensors.

4. A testing device according to claim 3, wherein said network of microsensors is a network of radiation microsensors organized in a matrix of lines and columns.

5. A testing device according to claim 4, wherein interface electronics are placed at an end of the radiation microsensor lines or at an end of the radiation microsensor columns.

6. A testing device according to claim 3, wherein each radiation microsensor includes a cell capable of transforming the radiation generated by the surface of said component into electrical charges in order to collect the electrical charges.

7. The device according to claim 3 wherein the means for measurement comprises a thermosensitive liquid crystal membrane, and the network of microsensors is a network of opto-electronic microsensors superimposed on the thermosensitive liquid crystal membrane.

8. A testing device according to claim 7, wherein said network of opto-electronic microsensors is organized in a matrix of lines and columns.

9. A testing device according to claim 8, wherein each opto-electronic microsensor comprises a photosensitive cell to transform the optical signals into electric signals, said cell being coupled to a charge transfer device to collect electric signals.

10. A testing device according to claim 8, wherein interface electronics are placed at an end of the opto-electronic microsensor lines or at an end of the opto-electronic microsensor columns.

11. A testing device according to claim 3, wherein said microsensors are about one hundred microns in size.

12. A testing device according to claim 1, wherein said device also comprises interface electronics connecting said means for measurement to a recording memory.

13. A testing device according to claim 12, wherein said interface electronics and said memory are incorporated into said flexible housing so as to form a monolithic testing device.

14. A testing device according to claim 12, wherein said testing device includes a calculating system.

15. A testing device according to claim 14, comprising a means of transmission for sending electrical signals recorded in the recording memory to said calculating system by using a radio or infrared wired or wireless link.

16. A testing device according to claim 14, wherein said calculating system is incorporated into said flexible housing and is connected between said interface electronics and said recording memory.

17. A testing device according to claim 16, wherein at least one map of the reference radiation field is predetermined through modeling.

18. A testing device according to claim 14, wherein said calculating system comprises:
 a memory comprising at least one reference map of a reference radiation field of the component,
 a means for calculation for converting electrical signals representing the radiation field generated by the surface of the component, and
 means for analysis of said radiation field generated by the surface of the component through comparison with the reference radiation field.

19. A testing device according to claim 18, wherein at least one map of the reference radiation field is predetermined from a reference structure.

20. A testing device according to claim 18, wherein said means for analysis includes a means for differential analysis to determine whether the radiation field generated by the surface of the component is elevated.

21. A testing device according to claim 20, wherein said means of differential analysis includes a means of generating a status state S when said radiation field generated by the surface of the component exceeds a threshold value.

22. A testing device according to claim 21, wherein said means of analysis includes a means of spectral analysis to determine information relative to defects present in the component.

23. A testing device according to claim 22, wherein said status signal S and said information are transmitted by said calculating system to an alarm means.

24. A testing device according to claim 23, wherein said status signal S and said information are recorded in said recording memory connected to said calculating system, then transmitted to the alarm means using a radio or infrared wired or wireless link.

25. A testing device according to claim 23, wherein said alarm means includes a means of display and light or sound indicators.

26. A testing device according to claim 1, wherein a thickness of said testing device is less than or equal to 50 µm.

27. A testing device according to claim 1, wherein said flexible housing of the testing device is fixed to the surface of the component to be tested, by means of an adhesive material.

28. A testing device according to claim 1, wherein said microsensors are directly integrated into a lining layer for covering the surface of the component to be tested.

* * * * *